(12) United States Patent
Zemtsov (10) Patent No.: US 11,224,618 B2
(45) Date of Patent: Jan. 18, 2022

(54) FORMULATIONS AND METHODS FOR TREATMENT OF ACNE AND INFLAMMATORY SKIN CONDITIONS

(71) Applicant: Zemtsov Enterprises, LLC, Yorktown, IN (US)

(72) Inventor: Alexander Zemtsov, Yorktown, IN (US)

(73) Assignee: ZEMTSOV ENTERPRISES, LLC, Yorktown, IN (US)

( * ) Notice: Subject to any disclaimer, the term of this patent is extended or adjusted under 35 U.S.C. 154(b) by 954 days.

(21) Appl. No.: 14/394,705

(22) PCT Filed: Mar. 17, 2013

(86) PCT No.: PCT/US2013/032727
§ 371 (c)(1),
(2) Date: Oct. 15, 2014

(87) PCT Pub. No.: WO2013/158318
PCT Pub. Date: Oct. 24, 2013

(65) Prior Publication Data
US 2015/0093445 A1    Apr. 2, 2015

Related U.S. Application Data

(60) Provisional application No. 61/725,761, filed on Nov. 13, 2012, provisional application No. 61/624,725, filed on Apr. 16, 2012.

(51) Int. Cl.
| | | |
|---|---|---|
| A61K 35/57 | (2015.01) | |
| A61K 9/06 | (2006.01) | |
| A61K 31/495 | (2006.01) | |
| A61K 31/203 | (2006.01) | |
| A61K 9/00 | (2006.01) | |
| A61K 45/06 | (2006.01) | |
| A61K 31/573 | (2006.01) | |
| A61K 47/44 | (2017.01) | |
| A61K 31/197 | (2006.01) | |
| A61K 31/20 | (2006.01) | |
| A61K 31/201 | (2006.01) | |
| A61K 31/202 | (2006.01) | |
| A61K 47/10 | (2017.01) | |
| A61K 47/14 | (2017.01) | |
| A61K 31/57 | (2006.01) | |
| A61K 31/4168 | (2006.01) | |

(52) U.S. Cl.
CPC ............ *A61K 35/57* (2013.01); *A61K 9/0014* (2013.01); *A61K 9/06* (2013.01); *A61K 31/197* (2013.01); *A61K 31/20* (2013.01); *A61K 31/201* (2013.01); *A61K 31/202* (2013.01); *A61K 31/203* (2013.01); *A61K 31/4168* (2013.01); *A61K 31/495* (2013.01); *A61K 31/57* (2013.01); *A61K 31/573* (2013.01); *A61K 45/06* (2013.01); *A61K 47/10* (2013.01); *A61K 47/14* (2013.01); *A61K 47/44* (2013.01)

(58) Field of Classification Search
CPC ..... A61K 35/57; A61K 31/203; A61K 31/495
See application file for complete search history.

(56) References Cited

U.S. PATENT DOCUMENTS

| | | |
|---|---|---|
| 4,772,591 A | 9/1988 | Meisner |
| 5,431,924 A | 7/1995 | Ghosh et al. |
| 5,472,713 A | 12/1995 | Fein et al. |
| 5,744,128 A | 4/1998 | Holick |
| 5,958,384 A | 9/1999 | Holick |
| 6,103,246 A | 8/2000 | Tisdale et al. |
| 6,342,208 B1 | 1/2002 | Hyldgaard et al. |
| 6,667,026 B1 | 12/2003 | Goldman et al. |
| 6,720,001 B2 | 4/2004 | Chen et al. |
| 6,790,847 B2 | 9/2004 | Walch |

(Continued)

FOREIGN PATENT DOCUMENTS

| | | |
|---|---|---|
| EP | 1637135 A1 | 3/2006 |
| KR | 20100005538 A * | 1/2010 |

(Continued)

OTHER PUBLICATIONS

Whitehouse et al. Emu oil(s): a source of non-toxic transdermal anti-inflammatory agents in aboriginal medicine. Inflammopharmacology. 6(1):1-8. (Year: 1998).*
Ash, et al. "Handbook of Preservatives". Nipagin N. p. 165. (Year: 2004).*
Zemtsov, A, A Novel Vehicle Formulation for Treatment of Inflammatory Skin Diseases, Journal of Cosmetics, Dermatological Sciences and Applications, Jan. 1, 2013, pp. 18-21, vol. 3, No. 1.
Extended European Search Report, EP 13778264.5, dated Feb. 11, 2015, 8 pages.
Extended European Search Report, EP 13777719.9, dated Feb. 11, 2015, 9 pages.

(Continued)

*Primary Examiner* — Amy L Clark
(74) *Attorney, Agent, or Firm* — Reichel Stohry Dean LLP; Mark C. Reichel; Natalie J. Dean (57) ABSTRACT

Topically administrable compositions and methods for treating skin conditions in mammals, such as acne, rosacea, keratosis pilaris, photo-aging, and photo-rejuvenation. The composition includes a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more of these, and emu oil product selected from the group consisting of emu oil, a biologically active fraction of emu oil, and a combination of these. The composition further includes a therapeutic amount of topical retinoid. The combination of non-sedating antihistamine and retinoid with emu oil has been found to produce a synergistic effect that is more effective in the treatment of skin conditions than the compound used separately.

1 Claim, 3 Drawing Sheets

(56) References Cited

U.S. PATENT DOCUMENTS

| | | |
|---|---|---|
| 7,316,820 B2 | 1/2008 | Jordan |
| 8,114,385 B2 | 2/2012 | Tamarkin et al. |
| 8,128,947 B2 | 3/2012 | Jones et al. |
| 8,232,317 B2 | 7/2012 | Gan et al. |
| 2003/0129209 A1 | 7/2003 | Walch |
| 2003/0212078 A1 | 11/2003 | Klein |
| 2004/0132743 A1 | 7/2004 | Reddy et al. |
| 2004/0185115 A1 | 9/2004 | Pearson et al. |
| 2004/0198743 A1 | 10/2004 | Hey et al. |
| 2004/0208860 A1 | 10/2004 | Farmer |
| 2004/0241197 A1 | 12/2004 | Biergiesser et al. |
| 2004/0266787 A1 | 12/2004 | Reddy et al. |
| 2005/0176732 A1 | 8/2005 | Cossement et al. |
| 2005/0182070 A1 | 8/2005 | Gobert |
| 2005/0238597 A1 | 10/2005 | McCook et al. |
| 2007/0079447 A1 | 4/2007 | Kroepke et al. |
| 2007/0207222 A1 | 9/2007 | Yu et al. |
| 2008/0025929 A1 | 1/2008 | Burton et al. |
| 2008/0124381 A1 | 5/2008 | Barnhart et al. |
| 2008/0208179 A1 | 8/2008 | Chan et al. |
| 2008/0255103 A1 | 10/2008 | Aslam et al. |
| 2009/0053290 A1 | 2/2009 | Sand et al. |
| 2009/0068128 A1 | 3/2009 | Waddington |
| 2009/0176792 A1 | 7/2009 | Gant et al. |
| 2009/0304812 A1 | 12/2009 | Staniforth et al. |
| 2010/0008868 A1 | 1/2010 | Dugger |
| 2010/0055161 A1 | 3/2010 | Ahn |
| 2010/0063008 A1 | 3/2010 | Matteliano et al. |
| 2010/0203122 A1 | 8/2010 | Weyer et al. |
| 2010/0221194 A1 | 9/2010 | Loupenok |
| 2011/0104159 A1 | 5/2011 | Rohrs et al. |
| 2012/0027876 A1 | 2/2012 | Ford |
| 2012/0045486 A1 | 2/2012 | Bravo Cordero et al. |
| 2012/0064011 A1 | 3/2012 | Schumann |
| 2012/0183588 A1 | 7/2012 | Supamahitorn et al. |
| 2012/0315235 A1 | 12/2012 | Weisenfluh |
| 2013/0115202 A1 | 5/2013 | Theoharides |

FOREIGN PATENT DOCUMENTS

| | | |
|---|---|---|
| WO | 92/08470 | 5/1992 |
| WO | 96/34596 | 11/1996 |
| WO | 98/33474 | 8/1998 |
| WO | 200113956 A2 | 3/2001 |
| WO | 01/87236 | 11/2001 |

OTHER PUBLICATIONS

Extended European Search Report, EP 13777761.1, dated Feb. 11, 2015, 8 pages.

International Search Report and Written Opinion for PCT/US13/32727 dated Jun. 10, 2013, 17 pages.

International Preliminary Report on Patentability for PCT/US13/32727 dated Nov. 1, 2013, 5 pages.

\* cited by examiner

FORMULATIONS AND METHODS FOR TREATMENT OF ACNE AND INFLAMMATORY SKIN CONDITIONS

PRIORITY

The present application is a U.S. National Phase of International PCT Application No. PCT/US13/32727 filed on Mar. 17, 2013, and is also related to, and claims the priority benefit of, U.S. Provisional Patent Application Ser. Nos. 61/624,725, filed Apr. 16, 2012, and 61/725,761, filed Nov. 13, 2012, each of which is hereby incorporated by reference in their entirety into this disclosure.

BACKGROUND

The emu (*Dromiceius novae*-hollandiae) is the second largest member of the group of flightless birds and is indigenous to Australia. Emus can be raised like ordinary farm animals and used for their valuable products, which include very low fat meat, supple leather hides, decorative and nutritional eggs, and rich oil. Emu oil may be extracted or rendered from the body fat of the emu and is known to contain triglyceride esters of long-chain saturated and unsaturated fatty acids, including oleic acid, linoleic acid, palmitic acid, and stearic acid.

Atopic dermatitis and other forms of eczema are inflammatory, pruritic (i.e., itchy) skin diseases that affect between 10 and 20 percent of the United States (U.S.) population, causing considerable morbidity, poor quality of life, and high medical costs for both the patient and society. Topically administered glucocorticoids are a main form of therapy; however, prolonged use of topical glucocorticoids is associated with skin thinning, permanent stretch marks, dermal atrophy, rebound effects, tachyphylaxis, and potential systemic absorption, which can cause numerous systemic side effects. Topical calcineurin inhibitors (e.g., Elidel® and Protopic® creams and ointments) are effective but are infrequently used as a result of FDA-required "black box" warnings concerning a potential increase in systemic malignancies in patients using these topical preparations.

Psoriasis is also a chronic pruritic inflammatory skin disease affecting 2% of the U.S. population. Inflammation and tumor necrosis factor-alpha ("TNF-alpha") are of crucial importance in the pathogenesis of psoriasis and its treatment. Based on the severity of the disease presentation, topical glucocorticoids, and vitamin D analogs, either by themselves or in combination with phototherapy or systemic agents (such as methotrexate, cyclosporine A, Humira®, Stelara®, Soriatane®, etc.), have been used for therapy. However, these agents can be extremely expensive, costing more than $20,000 per year per patient.

Acne vulgaris (i.e., cystic acne or, simply, acne), like psoriasis, atopic dermatitis, and other forms eczema, is considered an inflammatory disease, which is characterized by areas of skin with seborrhea (scaly red skin), closed comedones (i.e., "black heads"), open comedones (i.e., "white heads"), papules (pinheads), pustules (pimples), nodules (large papules), and possibly scarring. More specifically, acne is a disease of the pilosebaceous units, skin structures consisting of a hair follicle and its associated sebaceous gland. Propionibacterium acnes bacteria play a crucial role in pathogenesis of acne and can cause inflammation, progression of closed comedones (i.e., "black heads") to open comedones (i.e., "white heads") and to deep, painful acne cysts. Various topical and systemic antibacterial and anti-inflammatory agents have been used to mitigate these effects. Such antibacterial agents include clindamycin and tetracyclines, and anti-inflammatory agents such as dapsone and azelaic acid have been used.

Where application of topical steroids is a common therapy for eczema and psoriasis, the application of retinoids is a cornerstone of acne therapy because retinoids prevent clogging of hair follicles and the formation of closed comedones. However, all retinoids can produce severe skin irritation, known as retinoid dermatitis, that limits their utility and patient compliance in the treatment of acne. Consequently, retinoids are often combined with other anti-inflammatory compounds or moisturizing agents to minimize the incidence of retinoid dermatitis. Nonetheless, in the past 30 years only one new drug, dapsone, has been approved for the treatment of acne.

Histamine is a compound involved in local immune responses of humans and other animals. As part of an immune response to foreign pathogens, histamine is produced by basophils and mast cells found in nearby connective tissues. Upon release from these cells, histamines produce increased vascular permeability, causing fluid to escape from capillaries into tissues, which can lead to inflammation and itchiness, among other responses. Histamine triggers an immune system response by combining with specific cellular histamine receptors. The four histamine receptors that have been discovered in humans and animals are designated $H_1$ through $H_4$. Compounds, known as antihistamines, have been developed that do not prevent the release of histamine but instead inhibit the action of histamine by blocking it from attaching to the histamine receptors. Most commonly used antihistamines inhibit action specifically at the $H_1$ receptor and are referred to as $H_1$ antihistamines. While some $H_1$ antihistamines have sedative side effects, so-called "second generation" or "non-sedating" antihistamines do not cross the blood-brain barrier and, thus, do not cause drowsiness. Further, not all $H_1$ antihistamines inhibit the inflammatory response that results from the release of histamine in humans.

Extensive investments of time and capital are required to obtain Federal Drug Administration (FDA) approval to sell and market a new drug. The cost of approval is one reason that only three topical dermatological drugs were approved by the FDA in the last five years. Instead, pharmaceutical companies are primarily directing their efforts to develop and patent new delivery systems and formulations to more efficiently carry active ingredients (i.e., drugs) through the stratum corneum skin barrier. These new formulations include solid lipid nanoparticles, liposomes and niosomes, transferosomes, ethosomes, cyclodextrins, and sol-gel microcapsules.

Accordingly, there is a need for an anti-inflammatory, anti-pruritic topical formulation that does not cause retinoid dermatitis for use in treating skin conditions in mammals.

BRIEF SUMMARY

According to one aspect of the present invention, a composition for the treatment of skin conditions is disclosed. In at least one embodiment, a topically administrable composition for treating skin conditions in mammals includes a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more thereof, and emu oil product selected from the group consisting of emu oil, a biologically active fraction of emu oil, and a combination thereof.

In at least one embodiment, the non-sedating antihistamine is selected from the group consisting of cetirizine, levocetirizine, loratadine, fexofenadine, rupatadine, acrivastine, ebastine, bilastine, and a combination of two or more thereof. The physiologically acceptable acid of the non-sedating antihistamine is selected from the group consisting of an acid of cetirizine, an acid of levocetirizine, an acid of loratadine, an acid of fexofenadine, an acid of rupatadine, an acid of acrivastine, an acid of ebastine, an acid of bilastine, and a combination of two or more thereof. The non-sedating antihistamine is selected from the group consisting of a salt of cetirizine, a salt of levocetirizine, a salt of loratadine, a salt of fexofenadine, a salt of rupatadine, a salt of acrivastine, a salt of ebastine, a salt of bilastine, and a combination of two or more thereof. The amide of a non-sedating antihistamine is selected from the group consisting of an amide of cetirizine, an amide of levocetirizine, an amide of loratadine, an amide of fexofenadine, an amide of rupatadine, an amide of acrivastine, an amide of ebastine, an amide of bilastine, and a combination of two or more thereof.

In at least one embodiment, the composition includes 0.1 to 5.0 wt.-% of the antihistamine and at least 75 wt.-% of the emu oil product. In at least one embodiment, the composition includes 2.0 wt.-% of the antihistamine, and at least 85 wt.-% of the emu oil product.

In at least one embodiment, the composition includes a therapeutic amount of topical retinoid. The topical retinoid is selected from the group consisting of retinol, retinal, tretinoin, isotretinoin, alitretinoin, etretinate, acitretin, tazarotene, bexarotene, adapalene, and a combination of two or more thereof. In at least one embodiment, the composition includes 0.01 to 1.0 wt.-% of the topical retinoid, 0.1 to 5.0 wt.-% of the antihistamine, and at least 75 wt.-% of the emu oil product. In at least one embodiment the composition includes 0.05 wt.-% of the topical retinoid, 2.0 wt.-% of the antihistamine, and at least 85 wt.-% of the emu oil product.

In at least one embodiment, the composition further includes a preservative, and a neutral emulsifying agent. In at least one embodiment, the composition includes 0.1 to 1.0 wt.-% of preservative. In at least one embodiment, the composition includes 0.2 wt.-% of preservative. In at least one embodiment, the preservative includes methylparaben and the emulsifying agent includes propylene glycol.

In at least one embodiment, the antihistamine is selected from the group consisting of cetirizine, a physiologically acceptable acid of cetirizine, a salt of cetirizine, an amide of cetirizine, and a combination of two or more thereof. In at least one embodiment, the antihistamine is selected from the group consisting of levocetirizine, a physiologically acceptable acid of levocetirizine, a salt of levocetirizine, an amide of levocetirizine, and a combination of two or more thereof. In at least one embodiment, the topical retinoid is tretinoin.

According to one aspect of the present invention, a method of treating skin conditions in mammals is disclosed. The method includes topically applying to the skin of a mammal a topically administrable composition including a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more thereof, and emu oil product selected from the group consisting of emu oil, a biologically active fraction of emu oil, and a combination thereof. The method further includes repeating the topical application of the composition as indicated for resolution or control of the skin condition. In at least one embodiment, the method includes applying a composition further including a topical retinoid.

According to one aspect of the present invention, a kit for treating skin conditions in mammals is disclosed. The kit includes a first composition, where the first composition includes a therapeutic amount of a first antihistamine selected from the group consisting of a first non-sedating antihistamine, a first physiologically acceptable acid of a non-sedating antihistamine, a first salt of a non-sedating antihistamine, a first amide of a non-sedating antihistamine, and a combination of two or more thereof, and a first emu oil product selected from the group consisting of emu oil, a biologically active fraction of emu oil, and a combination thereof. The kit further includes a second composition, where the second composition includes a therapeutic amount of a second antihistamine selected from the group consisting of a second non-sedating antihistamine, a second physiologically acceptable acid of a non-sedating antihistamine, a second salt of a non-sedating antihistamine, a second amide of a non-sedating antihistamine, and a combination of two or more thereof; a therapeutic amount of topical retinoid; and a second emu oil product selected from the group consisting of emu oil, a biologically active fraction of emu oil, and a combination thereof.

In at least one embodiment, a method of treating skin conditions in mammals includes topically applying to the skin of a mammal a topically administrable first composition that includes a therapeutic amount of a first antihistamine selected from the group consisting of a first non-sedating antihistamine, a first physiologically acceptable acid of a non-sedating antihistamine, a first salt of a non-sedating antihistamine, a first amide of a non-sedating antihistamine, and a combination of two or more thereof; a therapeutic amount of topical retinoid; and a first emu oil product selected from the group consisting of emu oil, a biologically active fraction of emu oil, and a combination thereof. The method further includes repeating the topical application of the first composition as indicated for resolution or control of the skin condition. The method further includes topically applying a topically administrable second composition that includes a therapeutic amount of a second antihistamine selected from the group consisting of a second non-sedating antihistamine, a second physiologically acceptable acid of a non-sedating antihistamine, a second salt of a non-sedating antihistamine, a second amide of a non-sedating antihistamine, and a combination of two or more thereof; and a second emu oil product selected from the group consisting of emu oil, a biologically active fraction of emu oil, and a combination thereof. The method further includes repeating the topical application of the second composition as indicated for one or more benefits, such benefits selected from the group consisting of control of the skin condition, prevention of recurrence of the skin condition, and avoiding side effects of the first composition. The method further includes topically applying the first composition as indicated to control recurrence of the skin condition.

In at least one embodiment, the first non-sedating antihistamine and the second non-sedating antihistamine are selected from the group consisting of cetirizine, levocetirizine, loratadine, fexofenadine, rupatadine, acrivastine, ebastine, bilastine, and a combination of two or more thereof. In at least one embodiment, the first acid of the non-sedating antihistamine and the second acid of the non-sedating antihistamine are selected from the group consisting of an acid of cetirizine, an acid of levocetirizine, an acid of loratadine, an acid of fexofenadine, an acid of rupatadine, an acid of acrivastine, an acid of ebastine, an acid of bilastine, and a combination of two or more thereof. In at least one embodiment, the first salt of the non-sedating antihistamine and the second salt of the non-sedating antihistamine are selected from the group consisting of a salt of cetirizine, a salt of levocetirizine, a salt of loratadine, a salt of fexofenadine, a salt of rupatadine, a salt of acrivastine, a salt of ebastine, a salt of bilastine, and a combination of two or more thereof. In at least one embodiment, the first amide of a non-sedating antihistamine and the second amide of a non-sedating antihistamine are selected from the group consisting of an amide of cetirizine, an amide of levocetirizine, an amide of loratadine, an amide of fexofenadine, an amide of rupatadine, an amide of acrivastine, an amide of ebastine, an amide of bilastine, and a combination of two or more thereof. In at least one embodiment, the first antihistamine and the second antihistamine are the same antihistamine.

In at least one embodiment, the first composition and the second composition each include 0.1 to 5.0 wt.-% of antihistamine and at least 75 wt.-% of the emu oil product. In at least one embodiment, the first composition and the second composition each include 2.0 wt.-% of antihistamine and at least 85 wt.-% of the emu oil product. In at least one embodiment, the first composition includes 0.01 to 1.0 wt.-% of the topical retinoid. In at least one embodiment, the first composition includes 0.05 wt.-% of topical retinoid. In at least one embodiment, the skin condition is selected from the group consisting of acne, rosacea, keratosis pilaris, photo-aging, photo-rejuvenation, and a combination of two or more thereof.

DETAILED DESCRIPTION

The present application discloses various formulations and methods for using the same for the treatment of skin conditions in mammals, such as acne, rosacea, keratosis pilaris, other inflammatory skin conditions, photo-aging, and photo-rejuvenation, without causing retinoid dermatitis. According to one aspect of the present disclosure, a treatment for acne, rosacea, and keratosis pilaris is disclosed. For the purposes of promoting an understanding of the principles of the present disclosure, reference will now be made to various embodiments and specific language will be used to describe the same. It will nevertheless be understood that no limitation of the scope of this disclosure is thereby intended, such alterations, modifications, and further applications of the principles of the disclosure being contemplated as would normally occur to one skilled in the art to which the disclosure relates.

A number of explanations and clinical trials are provided by way of explanation and not limitation. No theory of how the disclosure operates is to be considered limiting, whether proffered by virtue of description, comparison, or example. For the purposes of this disclosure, the term "emu oil" refers to lipid compositions, oils, and preparations of oils derived from the emu.

Emu oil, extracted or rendered from the body fat of the emu bird, has a number of beneficial properties for the treatment of skin conditions such as acne, rosacea, keratosis pilaris, other inflammatory skin conditions, photo-aging, and photo-rejuvenation. The beneficial properties of emu oil include that emu oil is noncomedogenic, antibacterial, moisturizing, anti-inflammatory, emulsifying, enhances transdermal penetration, and has a low potential for skin irritation. Taking each of these beneficial properties in turn, emu oil is noncomedogenic, meaning emu oil will not clog skin pores. Other such oils tend to clog pores in skin, which can result in the development of acne. Such oils include synthetic oils, like mineral oils, or animal oils, like mink or lard. Moreover, emu oil has been demonstrated to be antibacterial and moisturizing to skin. Bacterial secondary colonization and infection play important roles in the pathogenesis of atopic dermatitis, and the antibacterial properties of emu oil address this contributing factor. Further, moisturizers by themselves are therapeutic agents in the treatment of patients with psoriasis, atopic dermatitis, and other forms of eczema because moisturizers can improve skin hydration and normalize keratinocyte differentiation.

Emu oil has excellent skin barrier penetrating features and can enhance the transdermal penetration of active compounds, compounds otherwise unable to effectively treat disease beyond the epidermis. Emu oil is known to contain triglyceride esters of long-chain saturated and unsaturated fatty acids, including oleic acid, linoleic acid, palmitic acid, and stearic acid. Table 1 contains the typical chemical composition of emu oil which, being almost entirely triglyceride in nature, is a nearly completely neutral lipid. The transdermal penetration properties of emu oil are generally attributable to oleic acid, which enables penetration by fluidizing the intercellular lipids of the stratum corneum. However, studies of various long-chain fatty acids, including oleic acid, used as penetration enhancers have not reported a synergistic effect of using this particular property of emu oil with other active compounds as described herein.

Two other valuable properties of emu oil for a topical treatment delivery system are its emulsifying properties and low potential for irritation. Such emulsifying properties, absent the potential for irritation, enable emu oil to serve as both a carrier and an active compound in a formulation. In addition to the beneficial properties mentioned above, emu oil has anti-inflammatory properties. For example, topically administered emu oil has been shown to be as effective as orally administered, high-dose ibuprofen. Research suggests that at least some of emu oil's anti-inflammatory properties are due to TNF-alpha inhibition, which is a key target inflammatory molecule in systemic psoriasis therapy. Examples of prescription treatments for systemic psoriasis that operate by inhibiting TNF-alpha include Enbrel® and Humira®. However, prior to the present disclosure, no topical formulation with TNF-alpha inhibitory effects has been used to treat inflammatory or any other disease of the skin. Therefore, emu oil may act as a therapeutic agent for some skin conditions independent of any other active compound.

Certain of the beneficial properties of emu oil are most effective in treating specific types of skin conditions and less effective on others. Nonetheless, by combining emu oil with additional active compounds, the beneficial properties of emu oil may potentiate the therapeutic effects of both the emu oil and the additional active compounds. Accordingly, in at least one embodiment of the present disclosure, emu oil may be included in a formulation to dissolve one or more additional active compounds, carry the one or more additional active compounds through the skin barrier, and provide one or more therapeutic effects that are synergistically enhanced by the combination with the one or more additional active compounds.

In at least one embodiment according to the present disclosure, emu oil may be combined with a non-sedating antihistamine compound to treat various skin conditions such as acne, rosacea, keratosis pilaris, other inflammatory skin conditions such as psoriasis and atopic dermatitis, photo-aging, and photo-rejuvenation. One non-limiting example of a non-sedating antihistamine is cetirizine. Cetirizine is commonly used orally to treat hay fever, urticaria (i.e., hives), angioedema, and allergies. In addition to anti-allergic, bronchodiliatory, and antispasmodic properties, cetirizine has numerous pharmacological effects that are highly useful for the treatment of inflammatory skin conditions if used as a topical agent.

As a potent second-generation antihistamine, cetirizine has antipruritic properties that are very beneficial in treating inflammatory skin conditions, particularly atopic dermatitis, which has been described as a vicious cycle of itch-scratch-itch. In addition to relieving the symptoms of itch, antipruritic antihistamines help to prevent progression of the disease by suppressing the scratching impulse (i.e., the so-called Koebner phenomenon). Moreover, as a second-generation, non-sedating antihistamine, cetirizine has an excellent safety profile, which enables cetirizine (marketed as Zyrtec®) to be sold over-the-counter without a prescription. Further, cetirizine and its related isomers are unique among non-sedating antihistamines in that each has various anti-inflammatory properties useful for the treatment of inflammatory skin conditions. Namely, cetirizine inhibits expression of adhesion molecules in patients with both atopic dermatitis and psoriasis and inhibits both T lymphocytes and monocytes, which play a central role in the pathogenesis of atopic dermatitis and psoriasis. Finally, cetirizine exerts anti-inflammatory effects on neutrophils apart from $H_1$ antagonism and inhibits eosinophil-related skin inflammation.

The anti-inflammatory properties of cetirizine are distinct from its other $H_1$ antihistamine features. For example, diphenhydramine (marketed as Benadryl®) is specifically contraindicated to treat inflammatory skin disease, such as eczema and psoriasis. In fact, where sold in the United States, the packaging for diphenhydramine includes a warning label clearly stating that it should not be used on "raw or broken skin" or "areas producing discharge." Other commonly used non-sedating antihistamines that do not have anti-inflammatory properties include loratadine (marketed as Claritin®) and fexofenadine (marketed as Allegra®). Therefore, not all non-sedating, $H_1$ antihistamines are appropriate for the treatment of inflammatory skin conditions.

Though emu oil and cetirizine both have anti-inflammatory properties, each utilizes completely different biochemical pathways. Consequently, instead of enabling merely additive beneficial anti-inflammatory effects, the combination of emu oil and cetirizine provides a synergistic enhancement of the beneficial effects of both active compounds in treating inflammatory skin conditions. Furthermore, emu oil, in addition to being a therapeutic agent, also enables penetration of cetirizine into the skin, thereby improving the efficacy of cetirizine separate from the synergistic effect.

Cetirizine is a racemic 50/50 mixture of levocetirizine, which is the active enantiomer (or L-stereoisomer), and the much less biologically active enantiomer (or D-stereoisomer). Like cetirizine, levocetirizine is a non-sedating antihistamine that includes anti-inflammatory properties. Accordingly, in at least one embodiment of the present disclosure, emu oil may be combined with levocetirizine to treat skin conditions such as acne, rosacea, keratosis pilaris, other inflammatory skin conditions such as psoriasis and atopic dermatitis, photo-aging, and photo-rejuvenation. Other non-sedating, anti-inflammatory antihistamines include, but are not limited to rupatadine, acrivastine, ebastine and bilastine.

In at least one embodiment of the present disclosure, emu oil may be combined with a topical retinoid compound, such as a tretinoin, to treat skin conditions such as acne, rosacea, keratosis pilaris, other inflammatory skin conditions such as psoriasis and atopic dermatitis, photo-aging, and photo-rejuvenation. Non-limiting examples of retinoid compounds include retinol, retinal, tretinoin (retinoic acid), isotretinoin, alitretinoin, etretinate and its metabolite acitretin, tazarotene, bexarotene, and adapalene. Such retinoids activate retinoid acid ("RAR") nuclear receptors, which may act to modify gene expression, subsequent protein synthesis, and epithelial cell growth and differentiation. Generally, retinoids appear to influence the cell life cycle in the follicle lining, which helps to prevent the hyperkeratinization of these cells that can create a blockage. While effective topical retinoids have been in use for over 30 years, they are available only by prescription due to potential side effects and are not as widely used as the other topical treatments. However, in at least one embodiment of the present disclosure, non-prescription formulations including emu oil and relatively low concentrations of retinoids are disclosed.

Emu oil in combination with a topical retinoid may alleviate a number of indications of acne. For example, the antibacterial properties of emu oil are helpful in limiting or eliminating Propionibacterium acnes bacteria, which play a crucial role in pathogenesis of acne and can cause inflammation and progression of closed comedones to open comedones and to deep, painful acne cysts. Follicles infected with Propionibacterium acnes bacteria may itch mildly at times and strongly at others. Accordingly, the anti-inflammatory and antipruritic properties of emu oil may alleviate the inflammation and pruritisis associated with Propionibacterium acnes bacterial infection and acne generally. Moreover, the anti-inflammatory and antipruritic properties of emu oil may further reduce the incidence and severity of retinoid dermatitis, which is significant irritation of the skin caused by retinoids. As a further example, because emu oil is noncomedogenic, it is capable of operating as a dermal penetration enhancer and emulsifier for the retinoid without exacerbating the comedones the formulation is intended to treat.

In at least one embodiment of the present disclosure, emu oil may be combined with a topical retinoid compound and with a non-sedating antihistamine to treat various skin conditions such as acne, rosacea, keratosis pilaris, other inflammatory skin conditions such as psoriasis and atopic dermatitis, photo-aging, and photo-rejuvenation. Specifically, emu oil may be combined with a topical retinoid compound and with an anti-inflammatory, non-sedating antihistamine, such as cetirizine, to treat acne and other inflammatory skin conditions. In such a formulation, the anti-inflammatory, non-sedating antihistamine may potentiate the disclosed anti-inflammatory benefits of emu oil in further alleviating the inflammation associated with both Propionibacterium acnes bacterial infection and retinoid dermatitis. Accordingly, the synergistic combination of anti-inflammatory, non-sedating antihistamine and emu oil is capable of treating a cause of acne and reducing the incidence and severity of a side effect of the treatment, that being retinoid dermatitis. In addition, the anti-inflammatory, non-sedating antihistamine may potentiate the disclosed antipruritic benefits of emu oil in further alleviating the often pruritic nature of healing acne lesions. Thus, the combined anti-inflammatory and antipruritic properties of emu oil and the non-sedating antihistamine synergistically facilitate healing and resolution of acne by reducing an acne patient's "pick and scratch" impulse, which can aggravate acne and cause scaring.

In at least one embodiment according to the present disclosure, a first formulation 10 may contain by weight 75-100% emu oil, 0.1-5.0% non-sedating antihistamine, and 0.1-1.0% preservative, with the balance being a neutral emulsifying solvent. In at least one embodiment, the first formulation 10 may contain by weight 75-100% emu oil, 0.1-5.0% cetirizine, 0.1-1.0% methylparaben preservative, and the balance propylene glycol or other neutral emulsifying solvent. In at least one embodiment, the first formulation 10 may contain by weight at least 85% emu oil, 2.0% cetirizine, 0.2% methylparaben preservative, and the balance propylene glycol. In at least one embodiment, the first formulation 10 may contain by weight 75-100% emu oil, 0.1-5.0% levocetirizine, 0.1-1.0% methylparaben preservative, and the balance propylene glycol or other neutral emulsifying solvent. In at least one embodiment, the first formulation 10 may contain by weight at least 85% emu oil, 2.0% levocetirizine, 0.2% methylparaben preservative, and the balance propylene glycol.

In at least one embodiment according to the present disclosure, a second formulation 20 may contain by weight 75-100% emu oil, 0.1-5.0% non-sedating antihistamine, 0.01-1.0% topical retinoid, and 0.1-1.0% preservative, with the balance being a neutral emulsifying solvent. In at least one embodiment, the second formulation 20 may contain by weight 75-100% emu oil, 0.1-5.0% cetirizine, 0.01-1.0% tretinoin, 0.1-1.0% methylparaben preservative, and the balance propylene glycol or other neutral emulsifying solvent. In at least one embodiment, the second formulation 20 may contain by weight at least 85% emu oil, 2.0% cetirizine, 0.05% tretinoin, 0.2% methylparaben preservative, and the balance propylene glycol. In at least one embodiment, the second formulation 20 may contain by weight 75-100% emu oil, 0.1-5.0% levocetirizine, 0.01-1.0% tretinoin, 0.1-1.0% methylparaben preservative, and the balance propylene glycol or other neutral emulsifying solvent. In at least one embodiment, the second formulation 20 may contain by weight at least 85% emu oil, 2.0% levocetirizine, 0.05% tretinoin, 0.2% methylparaben preservative, and the balance propylene glycol.

Figure 1:
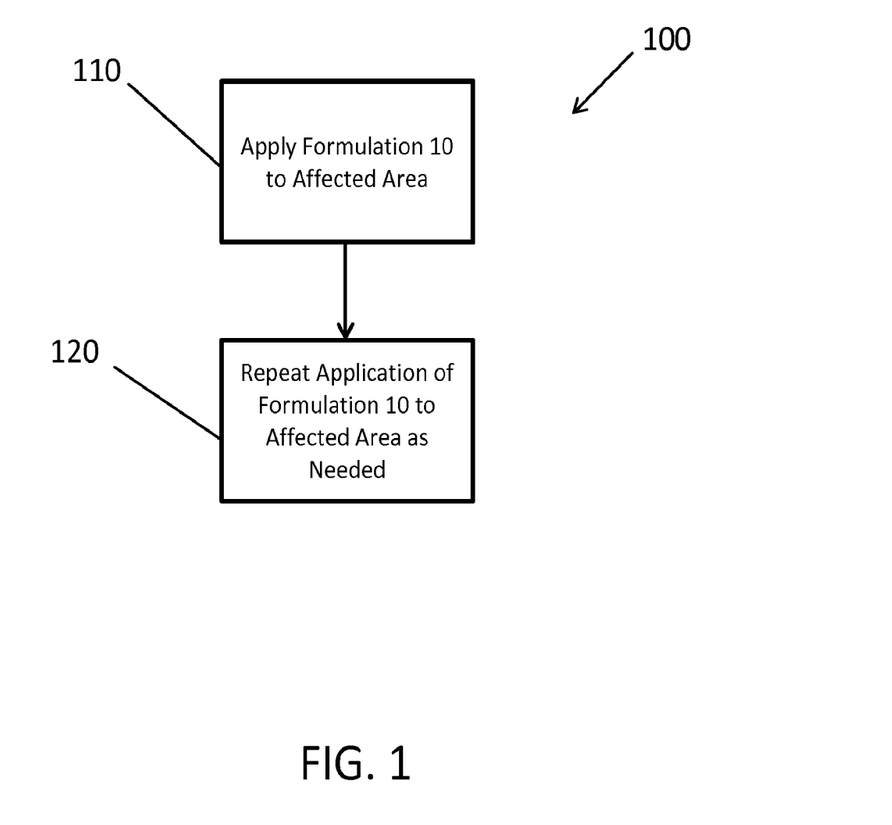
FIG. 1 shows a method of treating various skin conditions according to the present disclosure.
Figure 2:
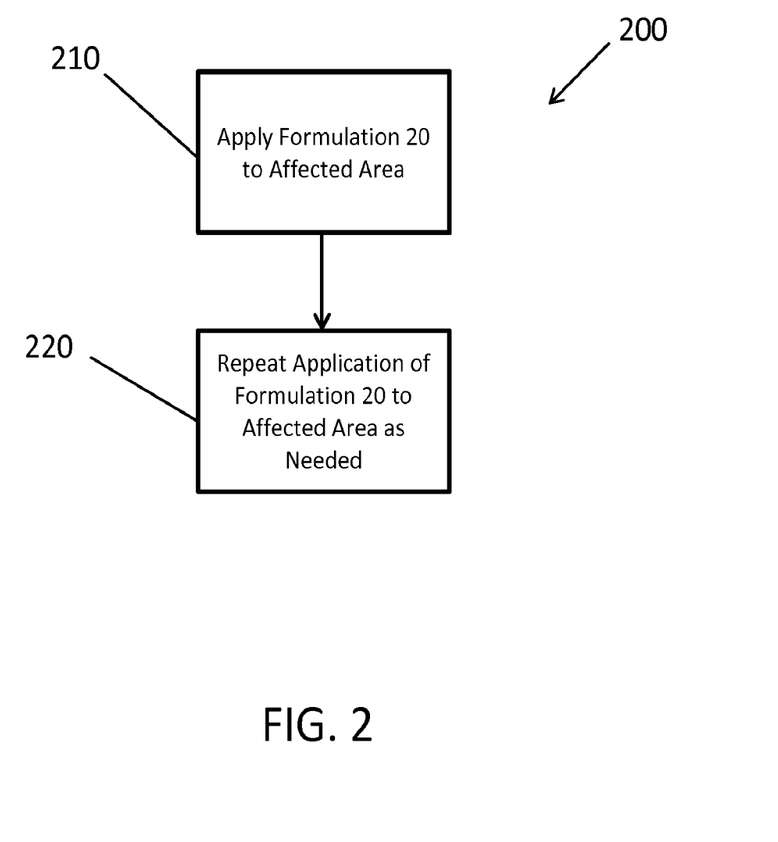
FIG. 2 shows a method of treating various skin conditions according to the present disclosure.

In one aspect of the present disclosure, the formulations disclosed herein may be used in a method 100 of treating skin conditions such as acne, rosacea, keratosis pilaris, other inflammatory skin conditions such as psoriasis and atopic dermatitis, photo-aging, and photo-rejuvenation as shown in FIG. 1. The method 100 may include a step 110 of applying the first formulation 10 to an affected area of skin. The method 100 may further include a step 120 of periodically repeating application of the first formulation 10 to the affected area of skin until the condition is resolved or controlled. Alternatively, a method 200 for treating skin conditions such as acne, rosacea, keratosis pilaris, other inflammatory skin conditions such as psoriasis and atopic dermatitis, photo-aging, and photo-rejuvenation is shown in FIG. 2. The method 200 may include a step 210 of applying the second formulation 20 to an affected area of skin. The method 200 may further include a step 220 of periodically repeating application of the second formulation 20 to the affected area of skin until the condition is resolved or controlled.

In one embodiment according to the present disclosure, a kit 50 may include a package, such as a tube, vial, dispenser, or other suitable container, of the first formulation 10 and a separate package of the second formulation 20. The kit 50 may be used with the methods described herein for the staged or pulsed treatment of acne and other inflammatory skin conditions. The kit 50 enables a physician to direct a patient to use the second formulation 20, including the combination of emu oil, non-sedating antihistamine, and topical retinoid, for a relatively short period of time and for localized areas to promote healing and clear active inflammatory lesions and then to use the first formulation 10, including the combination of emu oil and non-sedating antihistamine, as a moisturizer to prevent recurrence of the condition, thereby treating the skin condition while avoiding the side effects of chronic topical retinoid use described herein.

Figure 3:
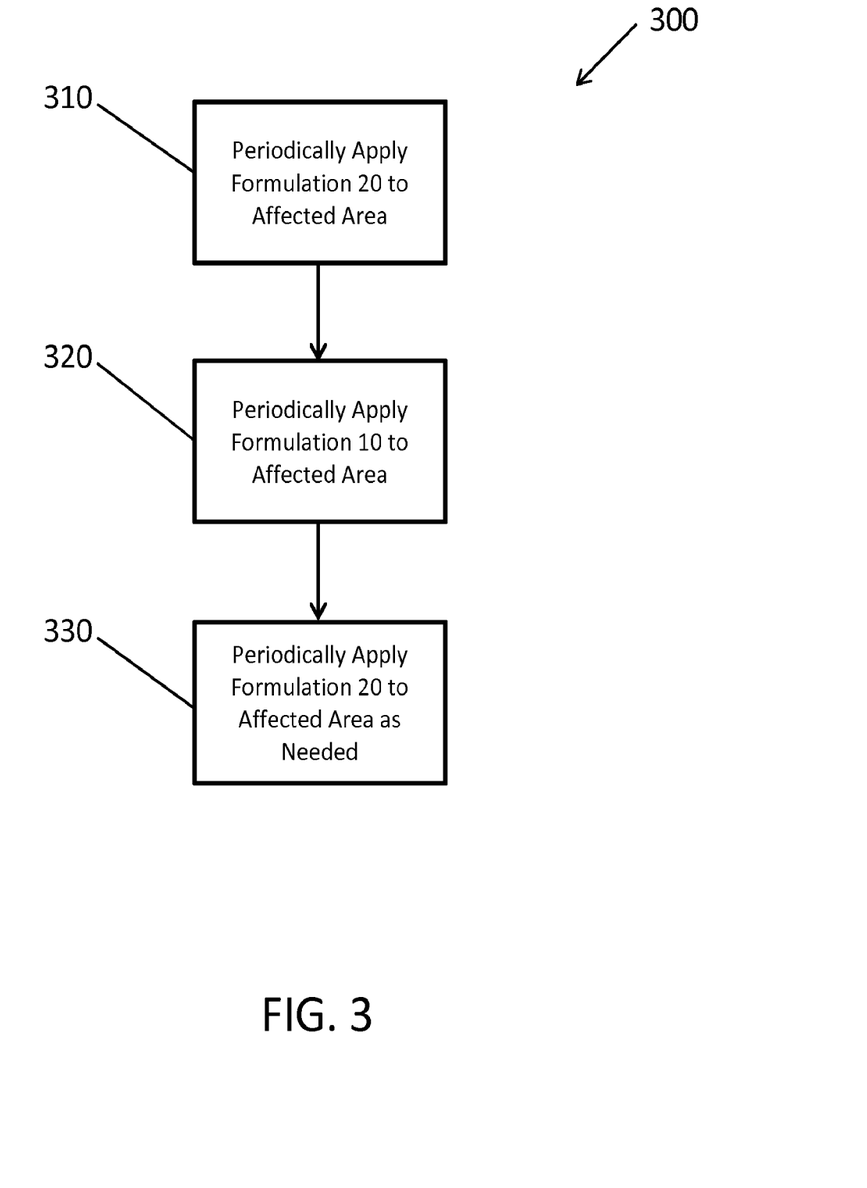
FIG. 3 shows a method of treating various skin conditions according to the present disclosure.

In one aspect of the present disclosure, one or more of the formulations disclosed herein, such as in the kit 50, may be used in a method 300 for treating skin conditions such as acne, rosacea, keratosis pilaris, other inflammatory skin conditions such as psoriasis and atopic dermatitis, photo-aging, and photo-rejuvenation as shown in FIG. 3. The method 300 may include a step 310 of periodically applying the second formulation 20 to an affected area of skin for a relatively short period of time. The period of time may be limited by a given patient's tolerance for the specific composition of the second formulation 20, by the sensitivity of the area of the patient's skin under treatment, or by resolution of the skin condition. The method 300 may further include a step 320 of periodically applying the first formulation 10 to an affected area of skin to avoid the side effects of chronic topical retinoid use described herein and to prevent recurrence of the condition. Optionally, the method 300 may include a step 330 of repeating the periodic application of the second formulation 20 to the affected area as required to maintain control of chronic disease. For example, the method 300 may include the application of the second formulation 20 (step 310) for two or three consecutive days, followed by the application of the first formulation 10 (step 320), and repeating (step 330) as needed to maintain control of a particular condition. Such alternating methods of therapy are commonly known as "pulse therapy."

The efficacy of combining emu oil with non-sedating antihistamine and with topical retinoid was determined by the following experiment. The following experiment is illustrative, but not limiting, of the methods and compositions of the present disclosure.

Other suitable modifications and adaptations of the variety of conditions and parameters normally encountered in clinical therapy and obvious to those skilled in the art, having the benefit of this disclosure, are within the scope of the present disclosure.

EXPERIMENT

In order to determine the efficacy of combining emu oil, a non-sedating antihistamine, and a topical retinoid as active compounds for the treatment of skin conditions such as acne and other inflammatory skin conditions, a single-blind clinical study was conducted. The study was designed to determine: (i) the efficacy of the active compounds in treating acne; (ii) whether the active compounds worked synergistically or simply provided additive effects; and (iii) the relative quantifiable effectiveness of each of the active compounds. As a single-blind study, ten research subjects received four tubes of preparations in cream form, labeled as A, B, C, and D, without knowledge of the formulations therein. However, a principal investigator and a study coordinator knew and recorded the formulations contained in each tube. Regarding the active compounds included in the study, Cream A included tretinoin and cetirizine in an emu oil base, Cream B included tretinoin in a propylene glycol base, Cream C included tretinoin in an emu oil base, and Cream D included tretinoin and cetirizine in a propylene glycol base. Each cream included an identical amount of tretinoin, namely 0.05% by weight. Further, each cream included methylparaben as a preservative and varying amounts of propylene glycol as a neutral emulsifying solvent. Cream B, which included only tretinoin as an active compound, was used as a control to provide a reference point for the degree of improvement observed for the other trial preparations. The study was conducted for six weeks.

To improve the statistical significance of the results, the study was designed as a comparative half/split face study. Specifically, each research subject applied each of the trial creams to the diseased skin on different locations on the subject's face. For example, a given subject applied Cream A to one side of the face and, on the identical abnormal skin on the opposite side of the face, applied either cream B, C, or D. Consequently, each research subject was his/her own positive and negative control. At the end of the study, each research subject completed a questionnaire specifically asking "which of the four creams worked the best" and asking the subject to numerically rate the efficacy of each cream on a scale of 1 (not effective) to 10 (extremely effective). The subjects' ratings were then multiplied by a factor of ten to enable simple percentage point comparisons between the trial creams. Moreover, each subject was asked to report any systemic or dermatological side effects of the creams, such as irritation, stinging, or pruritus.

The clinical response of each subject was assessed by the principal investigator, a physician trained, experienced, and Board Certified in dermatology, at the end of the 6-week study by comparing the condition of the subjects to a pre-trial evaluation on the same 1 to 10 scale used by the subjects. Similarly, the physician's evaluations were then multiplied by a factor of ten to enable simple percentage point comparisons between the trial creams. Finally, the study coordinator obtained clinical photographs of all areas treated at the beginning and end of the study.

The research subjects did not use any other prescription medication or over-the-counter topical preparation during the duration of the study. Informed written consent was obtained prior to initiation of the study from each research subject. No financial compensation was provided to any of the research subjects; however, each received a complimentary office visit and free medication. Further, at the end of the study, the subjects were offered and received a free complimentary tube of the cream of their choice (either cream A, B, C, or D). The subjects' clinical diagnoses included either psoriasis, atopic dermatitis, or stasis dermatitis. One subject withdrew from the study prior to its conclusion. Consequently, the evaluations of only nine subjects are included in the data.

Table 2 presents the physician's evaluations of the improvement or worsening of the research subjects' skin conditions by the end of the study, relative to the beginning of the study, for each of the trial creams A, B, C, and D. As shown Table 2, Cream A was rated most effective because it demonstrated the greatest improvement compared to creams B, C, and D, as reflected in the mean evaluation ratings across all subjects. Further, statistical analysis determined that the demonstrated improved effect of Cream A over the other creams was statistically significant (i.e., p<0.05). Table 2 further shows that Cream A was demonstrated to be 49% more effective than Cream B (i.e., the control) to a statistically significant degree as evaluated by the physician.

Table 2 includes a column of data for the "Additive Effect of Creams C & D" calculated for each subject based upon the physician's evaluations. The calculated additive effect of Cream C and Cream D was determined by, first, subtracting the rated effect of Cream B (the control) from the ratings given to Cream C and Cream D, which results in a value representing the beneficial effect of each cream in addition to the effect provided by Cream B. The resulting additional effects were then added together. Essentially, the calculated additive effect quantifies the combined effects of Cream C and Cream D, beyond the effect of the control cream, attributable to the active compounds operating separately. Thus, the calculated additive effect represents the expected or anticipated effect of combining and administering the three active compounds, tretinoin, cetirizine, and emu oil. On the other hand, the extent to which the rated effect of Cream A exceeds the calculated additive effect of Cream C and Cream D represents the unexpected and synergistic effect of combining and administering the three active compounds together. The synergistic effect may be calculated by subtracting the calculated additive effect of Cream C and Cream D from the rated evaluations for Cream A. Accordingly, Table 2 further includes the resulting unexpected and synergistic effect for each subject under column heading, "Synergistic Effect of Cream A," which contains the calculated percentage point improvement produced by the synergistic effect of Cream A beyond the simple additive effects of the active compounds administered separately via Cream C and Cream D.

As shown in Table 2, Cream A was on average 20% more effective than the net effects of Cream C and Cream D taken separately. Further, the synergistic effect was statistically significant. Because the ratings given to Cream A were statistically greater than the calculated additive effect of Cream C and Cream D, one may conclude that the combined effect of the active compounds included in Cream A exceeded the expected effect of these compounds acting separately by 20% on average. Therefore, the study unequivocally demonstrated that tretinoin, cetirizine, and emu oil synergistically potentiate each other's beneficial effects and that the synergistic effect is statistically significant. Furthermore, the study unequivocally demonstrated that emu oil and cetirizine synergistically potentiate each other's beneficial effects and that the synergistic effect is statistically significant.

Table 3 presents the research subjects' ratings of their own skin conditions at the end of the study, relative to the beginning of the study, for each of the trial creams A, B, C, and D. As shown in Table 3, the subjects' ratings generally corroborated the physician's evaluations. For example, each of the research subjects rated Cream A as the most effective for the treatment of his/her skin condition to a statistically significant degree. As shown in Table 3, Cream A was demonstrated to be 68% more effective than Cream B (the control) to a statistically significant degree as rated by the research subjects. In addition, Cream A was on average 28% more effective than the net effects of Cream C and Cream D taken separately, thereby demonstrating the synergistic effect of combining tretinoin, cetirizine, and emu oil as indicated by the subjects' ratings. Further, each research subject, at the end of the study, requested an additional free tube of Cream A only.

Certain individual results were of particular interest. For example, seven of the nine subjects remaining in the study had difficulty tolerating Cream B, which contained only tretinoin, due to the onset of retinoid dermatitis. Moreover, four subjects developed dermatitis in areas treated with Cream D, which contained cetirizine and tretinoin, while two subjects developed dermatitis in areas treated with Cream C, which contained emu oil and tretinoin. Thus, while the anti-inflammatory, moisturizing, and antipruritic effects of emu oil and cetirizine, taken separately, appeared to lower the incidence of retinoid dermatitis in the study, the combination of emu oil and cetirizine prevented any incidence of retinoid dermatitis in areas treated with Cream A. This result was unexpected by the principal investigator. Though the study was not designed to assess the ability of the combination of emu oil and cetirizine to treat retinoid dermatitis, the results of the study indicate a synergistic effect from combining emu oil and cetirizine to prevent retinoid dermatitis. Further, statistical analysis demonstrated that the synergistic effect was statistically significant.

In summary, the clinical study clearly demonstrated that the combination of a non-sedating antihistamine, a topical retinoid, and emu oil synergistically potentiates the mutually beneficial effects of the active compounds in treating skin conditions such as acne, rosacea, keratosis pilaris, and other inflammatory skin conditions, utilizing different biochemical pathways. Further, the study clearly demonstrated that the combination of a non-sedating antihistamine and emu oil synergistically inhibits the onset of retinoid dermatitis resulting from the use of a topical retinoid.

While various embodiments of a formulation for the treatment of skin conditions such as acne, rosacea, keratosis pilaris, other inflammatory skin conditions such as psoriasis and atopic dermatitis, photo-aging, and photo-rejuvenation and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and are therefore contemplated by the inventor. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

TABLE 1

Typical Emu Oil Fatty Acid Composition

| Fatty Acid | Percentage by Weight |
| --- | --- |
| Myristic | 0.4% |
| Palmitic | 21.5% |
| Palmitoleic | 3.7% |
| Stearic | 10.6% |
| Oleic | 51.4% |
| Linoleic | 12.7% |
| Linolenic | 0.9% |

TABLE 2

Physician Evaluations of Trial Creams

| Subject | Cream A | Cream B (Control) | Cream C | Cream D | Additive Effect of Creams C & D | Cream A Improvement over Control (%) | Synergistic Effect of Cream A (%) |
| --- | --- | --- | --- | --- | --- | --- | --- |
| 1 | 70 | 30 | 40 | 40 | 20 | 40 | 20 |
| 2 | 80 | 0 | 30 | 20 | 50 | 80 | 30 |
| 3 | — | — | — | — | — | — | — |
| 4 | 70 | 50 | 50 | 70 | 20 | 20 | 0 |
| 5 | 90 | 50 | 40 | 80 | 20 | 40 | 20 |
| 6 | 70 | 0 | 40 | 20 | 60 | 70 | 10 |
| 7 | 50 | 0 | 20 | 0 | 20 | 50 | 30 |
| 8 | 90 | 30 | 50 | 50 | 40 | 60 | 20 |
| 9 | 70 | 20 | 30 | 20 | 10 | 50 | 40 |
| 10 | 80 | 50 | 70 | 50 | 20 | 30 | 10 |
| Mean | 74 | 26 | 41 | 39 | 29 | 49 | 20 |

TABLE 3

Patient Ratings of Trial Creams

| Subject | Cream A | Cream B (Control) | Cream C | Cream D | Additive Effect of Creams C & D | Cream A Improvement over Control (%) | Synergistic Effect of Cream A (%) |
| --- | --- | --- | --- | --- | --- | --- | --- |
| 1 | 90 | 0 | 50 | 0 | 50 | 90 | 40 |
| 2 | 70 | 10 | 40 | 30 | 50 | 60 | 10 |

TABLE 3-continued

Patient Ratings of Trial Creams

| Subject | Cream A | Cream B (Control) | Cream C | Cream D | Additive Effect of Creams C & D | Cream A Improvement over Control (%) | Synergistic Effect of Cream A (%) |
|---|---|---|---|---|---|---|---|
| 3 | — | — | — | — | — | — | — |
| 4 | 50 | 0 | 0 | 0 | 0 | 50 | 50 |
| 5 | 100 | 30 | 40 | 40 | 20 | 70 | 50 |
| 6 | 50 | 20 | 30 | 40 | 30 | 30 | 0 |
| 7 | 50 | −50 | 20 | −50 | 70 | 100 | 30 |
| 8 | 70 | −20 | 20 | 10 | 70 | 90 | 20 |
| 9 | 90 | 30 | 50 | 40 | 30 | 60 | 30 |
| 10 | 70 | 10 | 40 | 20 | 40 | 60 | 20 |
| Mean | 71 | 3 | 32 | 14 | 40 | 68 | 28 |

The invention claimed is:

1. A topical composition for treating skin inflammation, the composition comprising:
  2.0% wt.-% of cetirizine;
  0.05% wt.-% of tretinoin;
  at least 85% wt.-% of emu oil;
  0.2% wt. % methylparaben; and
  the balance of propylene glycol.

* * * * *